(12) United States Patent
Sekine et al.

(10) Patent No.: US 7,760,349 B2
(45) Date of Patent: Jul. 20, 2010

(54) MASK-DEFECT INSPECTING APPARATUS WITH MOVABLE FOCUSING LENS

(75) Inventors: Akihiko Sekine, Tokyo (JP); Ikunao Isomura, Kawasaki (JP); Toshiyuki Watanabe, Kawasaki (JP); Shinji Sugihara, Kawasaki (JP); Riki Ogawa, Kawasaki (JP)

(73) Assignee: Kabushiki Kaisha TOPCON, Itabashi-ku, Tokyo (JP)

( * ) Notice: Subject to any disclaimer, the term of this patent is extended or adjusted under 35 U.S.C. 154(b) by 288 days.

(21) Appl. No.: 11/083,323

(22) Filed: Mar. 18, 2005

(65) Prior Publication Data
US 2005/0213084 A1  Sep. 29, 2005

(30) Foreign Application Priority Data
Mar. 22, 2004  (JP) .............................. 2004-081766

(51) Int. Cl.
*G01N 21/00*  (2006.01)
(52) U.S. Cl. .................................. 356/237.5; 356/237.4
(58) Field of Classification Search ....  356/237.1–237.6
See application file for complete search history.

(56) References Cited

U.S. PATENT DOCUMENTS

| | | | | |
|---|---|---|---|---|
| 4,920,385 | A * | 4/1990 | Clarke et al. ............. | 356/237.2 |
| 5,790,251 | A * | 8/1998 | Hagiwara .................. | 356/491 |
| 5,892,579 | A * | 4/1999 | Elyasaf et al. ........... | 356/239.8 |
| 5,991,039 | A * | 11/1999 | Fujishiro et al. ......... | 356/614 |
| 6,175,645 | B1 * | 1/2001 | Elyasaf et al. ............. | 382/147 |
| 6,184,976 | B1 * | 2/2001 | Park et al. ................ | 356/237.4 |
| 6,317,204 | B2 * | 11/2001 | Haga et al. ................ | 356/237.2 |
| 6,466,315 | B1 * | 10/2002 | Karpol et al. ............ | 356/237.4 |
| 2002/0171825 | A1 * | 11/2002 | Krantz et al. ............ | 356/237.1 |
| 2003/0179371 | A1 * | 9/2003 | Rangarajan et al. ...... | 356/237.2 |
| 2005/0002020 | A1 * | 1/2005 | Inoue et al. .............. | 356/237.1 |

FOREIGN PATENT DOCUMENTS

| | | |
|---|---|---|
| JP | 4-100045 | 4/1992 |
| JP | 5-216211 | 8/1993 |
| JP | 10-097053 A | 4/1998 |
| JP | 10-221266 | 8/1998 |
| JP | 11-237344 | 8/1999 |
| JP | 2002-039960 A | 2/2002 |
| JP | 2003-209043 A | 7/2003 |

OTHER PUBLICATIONS

Notice of Reason for Rejection issued in corresponding Japanese Patent Application No. 2004-081766, mailed Dec. 22, 2009, and English translation thereof.

* cited by examiner

*Primary Examiner*—Tarifur Chowdhury
*Assistant Examiner*—Tara S Pajoohi
(74) *Attorney, Agent, or Firm*—Buchanan Ingersoll & Rooney PC

(57) ABSTRACT

A mask-defect inspection apparatus including a plurality of illumination optical systems (2) for illuminating different areas (14a, 14b) on a mask (4) on which a pattern (6) is formed, an objective lens (OL) disposed to face the mask, and at least a pair of detection optical systems (15, 16) each having a detection sensor (17, 19) to form an image of the pattern and for receiving illumination light from each of the different areas through the objective lens, each of the detection optical systems having a mechanism (18a, 20a) for adjusting an angle of an aperture.

2 Claims, 11 Drawing Sheets

MASK-DEFECT INSPECTING APPARATUS WITH MOVABLE FOCUSING LENS

CROSS-REFERENCE TO THE RELATED APPLICATION

The application claims the priority benefit of Japanese Patent Application No. 2004-81766, filed on Mar. 22, 2004, the entire descriptions of which are incorporated herein by reference.

BACKGROUND OF THE INVENTION

1. Field of the Invention

The present invention relates to an improvement in a mask-defect inspecting apparatus for inspecting a defect, for example, braking, thinning, or adhesion of foreign matters, in a photo-mask used in the manufacture of a semi-conductor or a mask having a pattern formed on a sample of a glass wafer.

2. Description of Related Art

Conventionally, in an apparatus for inspecting a defect in a pattern formed on a photo-mask used for manufacturing a semiconductor, a chip on which a pattern is provided is observed by use of one detection optical system, and an image observed is compared with a reference image depending on design data to detect the defect of the photo-mask.

In addition, this kind of conventional apparatus for inspecting the mask defect includes a reflection-illumination optical system and a transmission-illumination optical system as the detection optical system to enable the defect in the mask to detect with higher sensitivity (for reference, see JP-A 10-97053).

Recently, in this kind of conventional apparatus for inspecting the mask defect, with a development in ministurization of semiconductor devices, a wavelength of illumination light used for exposure and inspection is significantly shortened, and deep-ultraviolet rays (DUV) have been used as the illumination light.

On the other hand, because the detection optical system used for the mask defect-inspection apparatus has a performance similar to a high-resolution microscope and uses an objective lens of a higher numerical aperture, it has higher resolving power, while has shallower depth of focus. As a result, the detection optical system has properties that the depth of focus becomes shallower as the wavelength of illumination light becomes shorter.

Therefore, this kind of conventional apparatus is designed to identify whether the detected defect corresponds mainly to the residue of the film-forming material or attachment of the foreign matter onto the mask by conducting the detection with fine adjustment of a focal plane of the detection optical system and by switching over an inspection carried out by the transmission-illumination light and an inspection carried out by the reflection-illumination light.

However, the conventional mask-defect inspecting apparatus of this type is on a tendency that the shortening of wavelength is called for and the depth of focus becomes shallower, while there is a tendency that a size in film thickness of the pattern in the mask as an object to be inspected is thicker. Accordingly, strict accuracy is demanded for the fine adjustment of the focal plane in the inspection of the transmission-illumination and the reflection-illumination, and also enlarging a range of the adjustment of the focal plane is demanded Therefore, there are troubles in prompt inspection and identification of the defect in the mask, in the conventional mask-defect inspecting apparatus.

SUMMARY OF THE INVENTION

An object of the present invention is to provide a mask-defect inspecting apparatus for inspecting a defect in a mask capable of achieving inspection for the mask at a time even if a film thickness of a pattern on a mask is thick despite a shortened wavelength of illumination light, and identification of kind of a defect in the mask easily.

According to an embodiment of the present invention, the mask-defect inspecting apparatus includes a plurality of illumination optical systems for illuminating different areas on a mask on which a pattern is formed, an objective lens disposed to face the mask, and at least a pair of detecting optical systems each having a detection sensor to form an image of the pattern and for receiving illumination light from each of the different areas through the objective lens.

Each of the detecting optical systems has a mechanism for adjusting an angle of an aperture.

BRIEF DESCRIPTION OF THE DRAWINGS

FIGS. 3A to 3C are diagrams for explaining types of masks, wherein FIG. 3A shows a state that a predetermined pattern is formed on a surface of a silica glass with a form-forming material, FIG. 3B shows a state that a pattern is formed on the surface of the silica glass with the film-forming material and a phase shifter, and FIG. 3C shows a state that a pattern is formed by providing the film-forming material on the surface of the silica glass and grooves on the surface.

FIGS. 4A to 4C show examples of defects generated on the mask, wherein FIG. 4A shows the thinning of the pattern, FIG. 4B shows a state that the film-forming material remains between the film-forming material and the film-forming material and FIG. 4C shows a state that a foreign matter is attached on a surface of the film-forming material.

FIGS. 5A to 5C show examples of defects on the mask as viewed from a cross-sectional direction, wherein FIG. 5A shows the foreign matter attached on the surface of the film-forming material FIG. 5B shows a state that foreign matters are attached on the surfaces of the silica glass and the phase shifter, and FIG. 5C shows a state that the foreign matter is attached on the groove and a residual of the film-forming material exists on the surface of the film-forming material.

DETAILED DESCRIPTION OF THE PREFERRED EMBODIMENTS

Preferred embodiments of the present invention will be explained in detail with reference to the accompanying drawings below.

Figure 1:
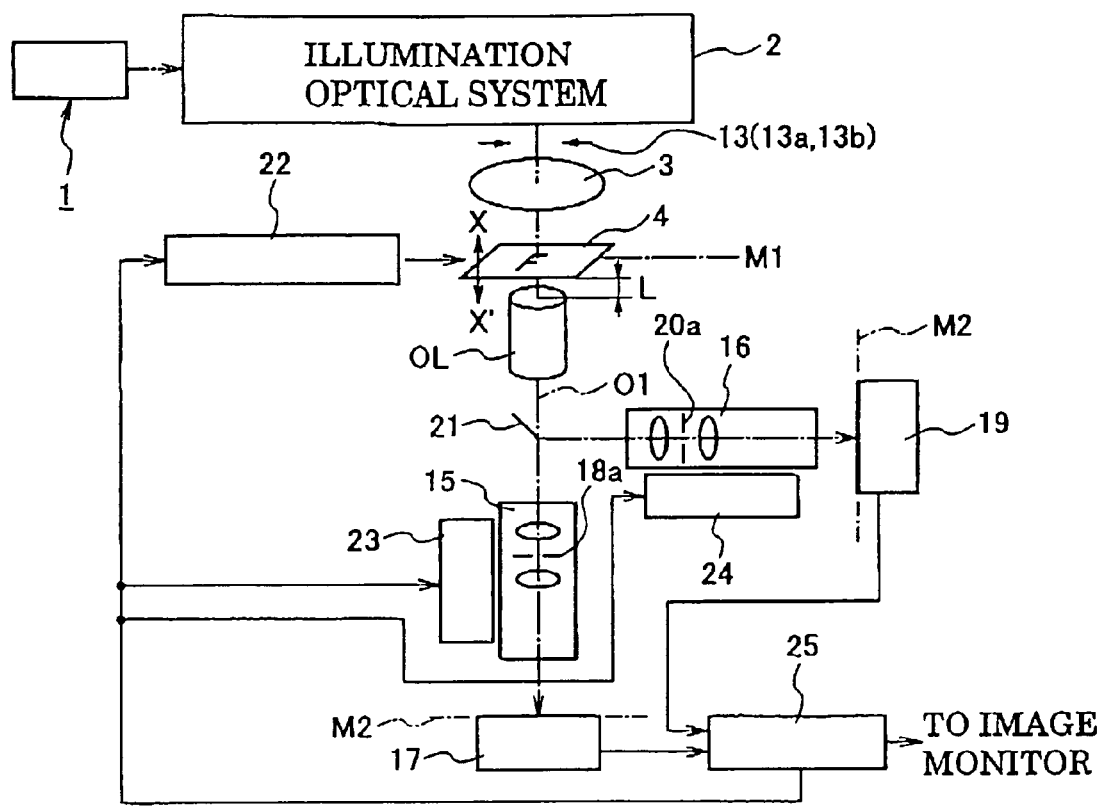
FIG. 1 is a diagram schematically showing an optical system in a first embodiment of a mask-defect inspecting apparatus according to the present invention.

FIG. 1 illustrates a first embodiment of a mask-defect inspecting apparatus according to the present invention. In FIG. 1, numeral 1 denotes a light source for illumination, 2 an illumination optical system, 3 a condenser lens, 4 a mask as a sample, and OL an objective lens.

Figure 2:
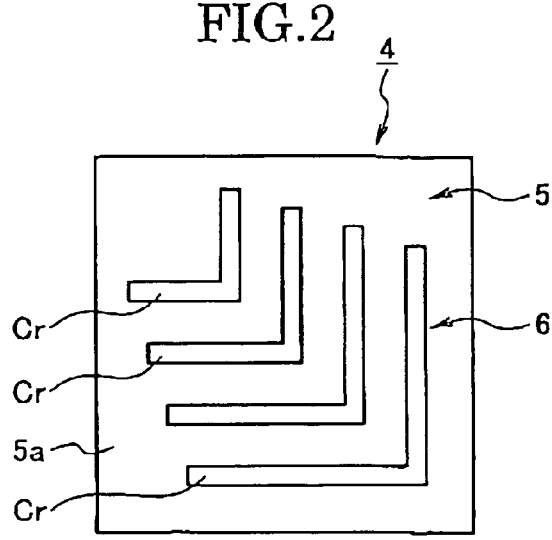
FIG. 2 is a diagram schematically showing one example of a pattern formed on a mask.

The mask 4 includes, for example, a transparent board 5 made of silica glass and a pattern 6 provided on a surface of the transparent board 5, as shown in FIG. 2 schematically. The pattern is made of Cr (chromium) as a material forming a film. There are provided various sectional structures in a thickness direction of the pattern 6 formed on the mask 4, as follows.

Figure 3A:
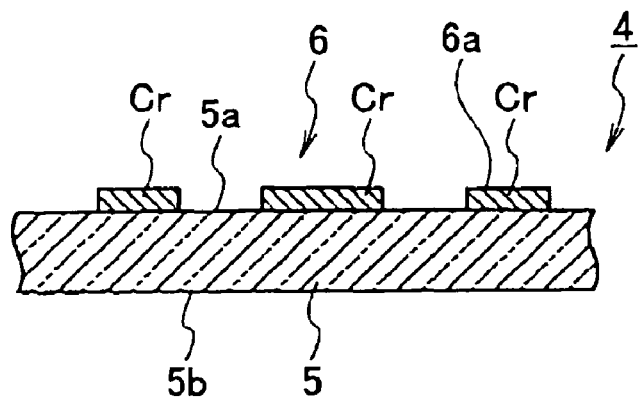

FIG. 3A illustrates a structure in which the pattern 6 is formed on a surface of the transparent board 5 of silica glass by providing a plurality of Cr films as the material for forming a film.

Figure 3B:
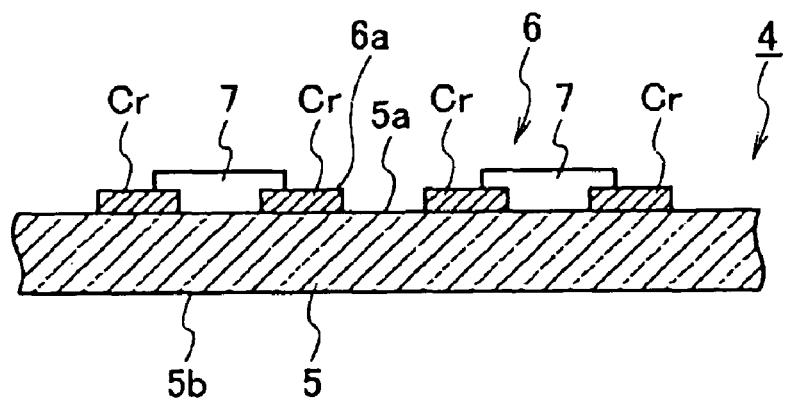

FIG. 3B illustrates a structure in which the pattern 6 is formed on the surface 5a of the transparent board 5 of silica glass by providing the Cr films spaced equally on the transparent board 5, and providing a phase shifter member 7 between the Cr films.

Figure 3C:
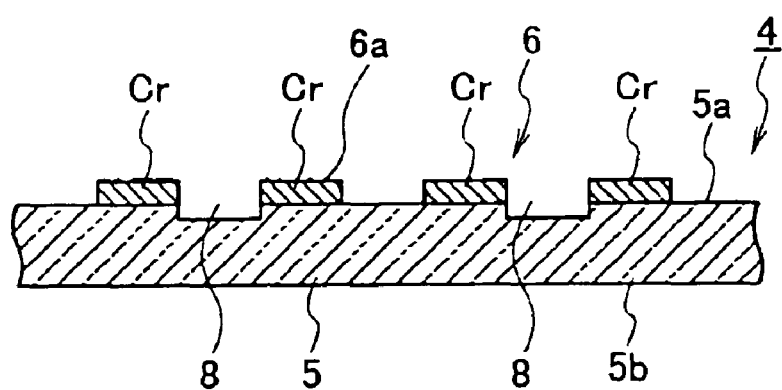

FIG. 3C illustrates a structure in which the pattern G is formed on the surface 5a of the transparent board 5 of silica glass by providing the Cr films spaced equally on the transparent board 5, and providing grooves 8 in the surface 5a of the transparent board 5.

Figure 4A:
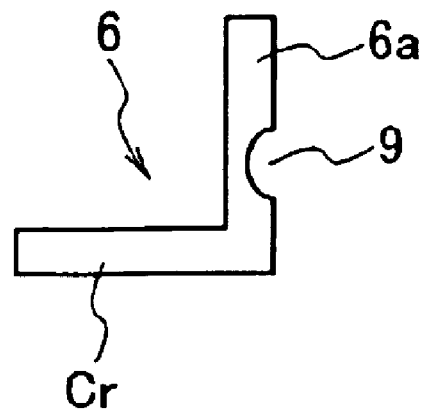
Figure 4B:
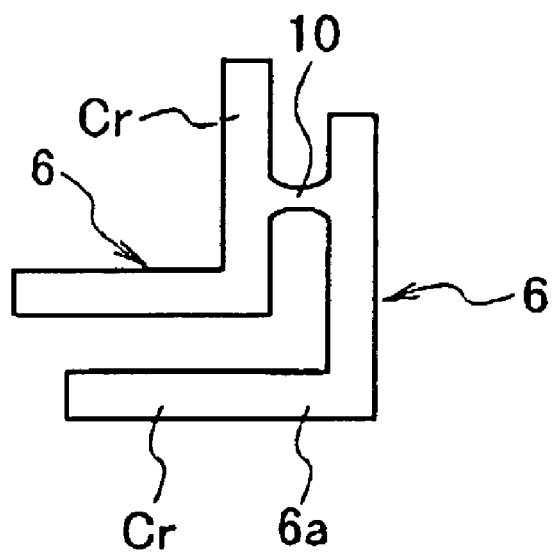
Figure 4C:
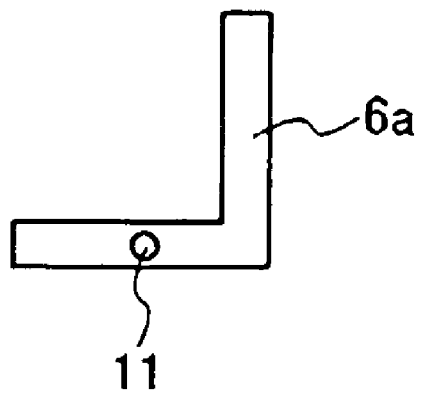

This kind of mask 4 is formed by depositing the Cr on the surface 5a of the transparent board of silica glass, applying a photo-resist, thereafter exposing a portion of the photo-resist, and removing the Cr by etching, and so on. There are often generated various defects in the mask 4, such as a defect 9 that a portion of the Cr forming the pattern 6 is removed, hence the pattern is thinned, as viewed from a top plan, as shown in FIG. 4A schematically, a defect 10 that the Cr as the film forming material remains in a state bridging the Cr films forming the pattern 6, as shown in FIG. 4B, and a defect 11 that the foreign matter adheres to a surface 6a of the Cr forming the pattern 6, as shown in FIG. 4C.

Figure 5A:
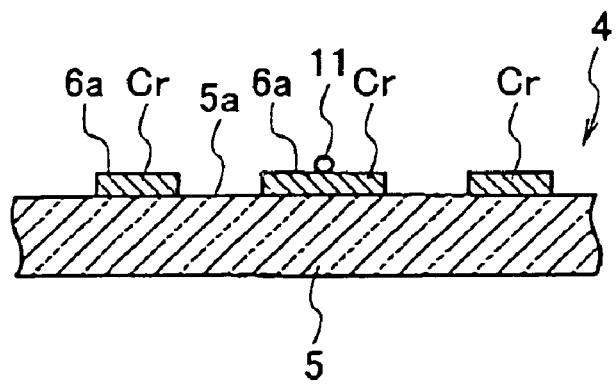
Figure 5B:
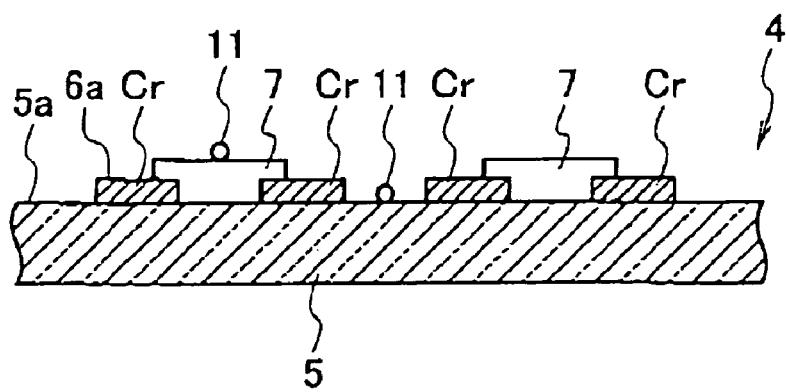
Figure 5C:
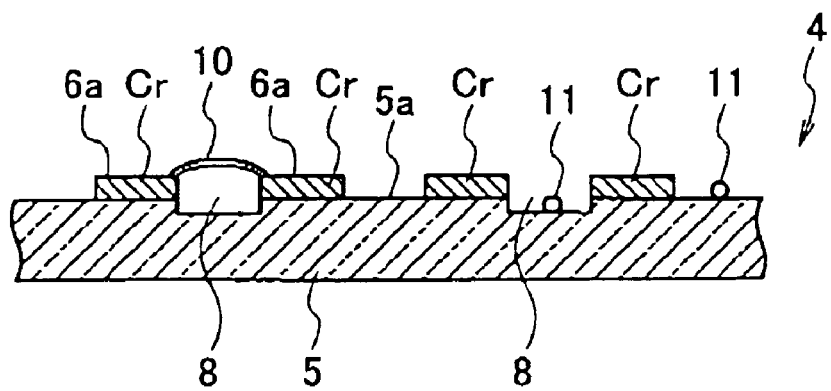

When viewing the defects by cutting the mask 4 in a thickness direction thereof, there are cases that for example, the defect 11 to which the foreign matter is adhered exists on the surface 6a of the Cr film 6, as shown in FIG. 5A, on a surface of the phase shifter member 7 or the surface 5a of the transparent member 5, as shown in FIG. 6B or in the groove 8, as shown in FIG. 5C, and the defect 10 remaining the film-forming material exists so as to bridge between the surfaces 6a of the adjacent Cr films without the surface 5a of the transparent member 5, as shown in FIG. 5C.

Laser is used as the illumination light source 1, and the illumination optical system 2 includes a laser coherent reduction mechanism and an integrator. A structure of the illumination optical system 2 is disclosed in JP 2002-39960A, and JP 2003-209043A, therefore a detailed description thereof is omitted.

The mask 4 is illuminated by a well-known Kohler illumination method using the condenser lens 3. As schematically shown in FIG. 6, the illumination light source 1 is once imaged as a light source image 1' on an anterior focal plane f1 of the condenser lens 3 by a light-focusing lens 12, and illumination light emitted from the anterior focal plane f1 illuminates the mask 4 as a parallel light flux P.

Figure 6:
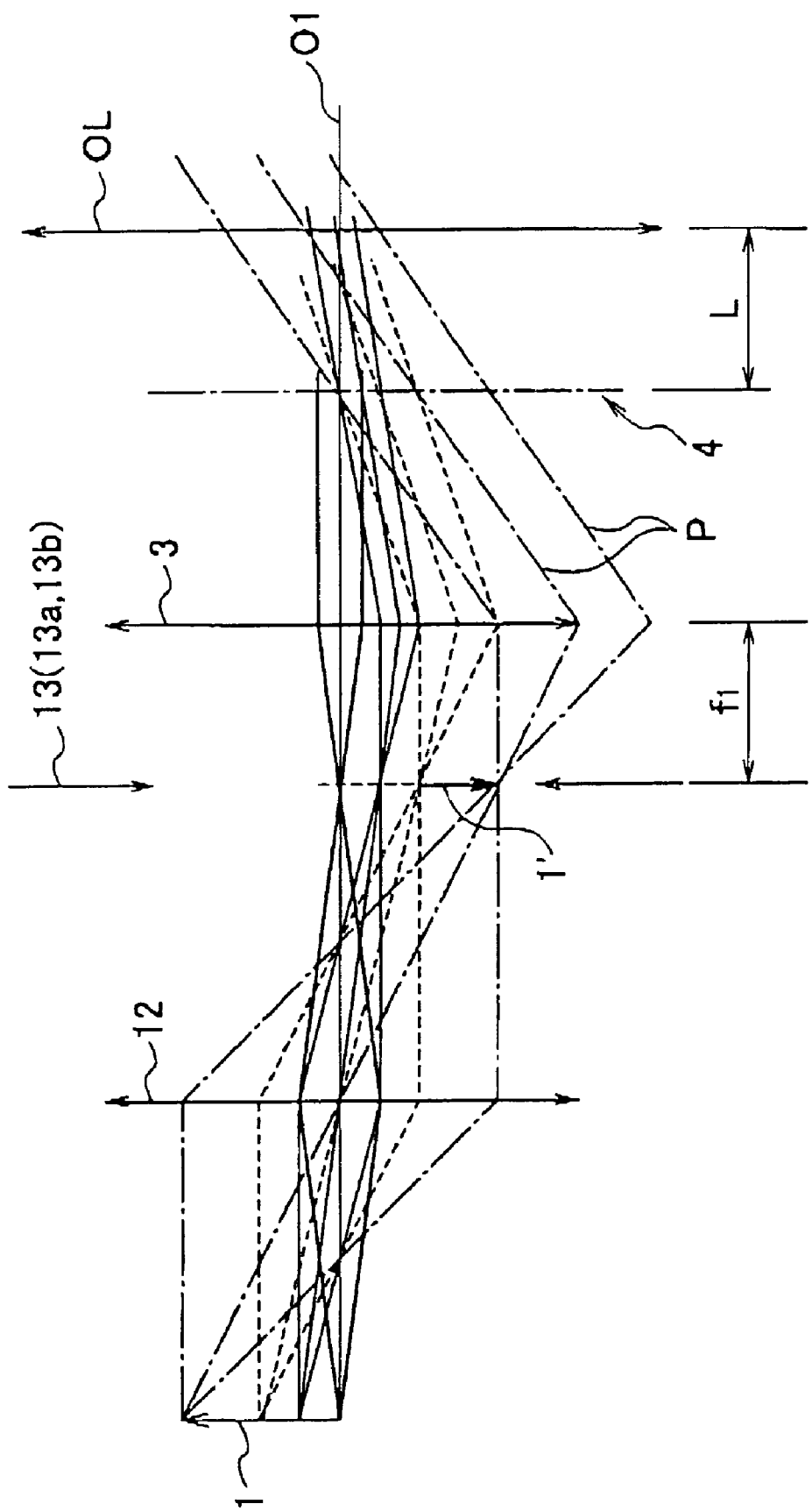
FIG. 6 is an optical diagram for explaining a general conception of an illumination optical system according to a Kohler illumination method.
Figure 7:
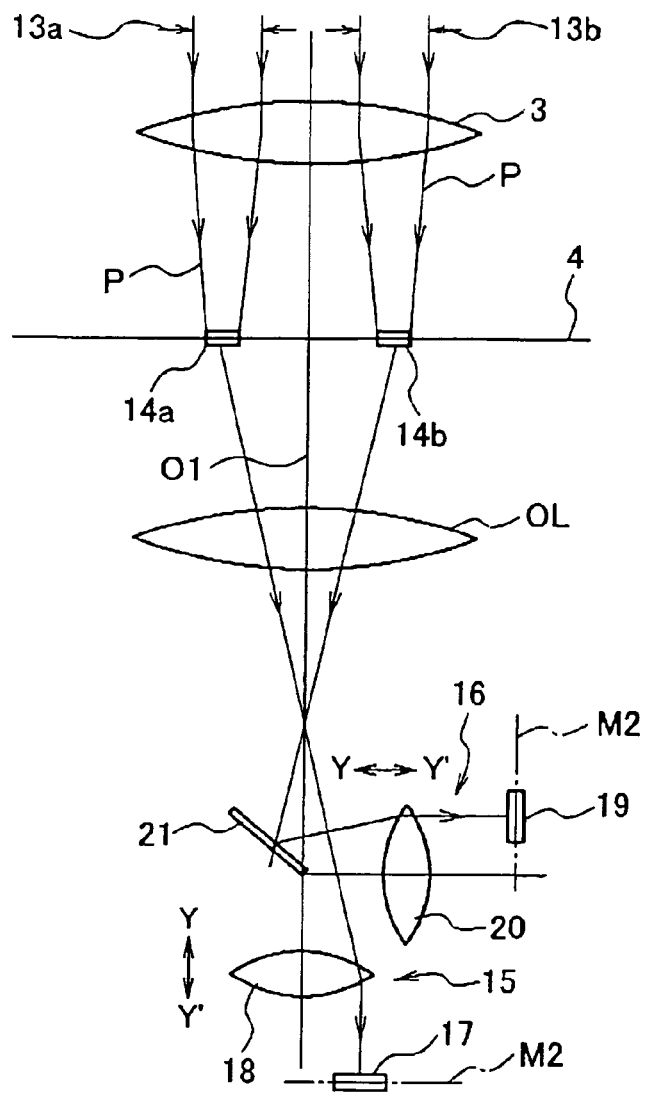
FIG. 7 is a diagram schematically showing different areas of the mask illuminated by the illumination optical system shown in FIG. 1 and a disposition relationship between detection optical systems and those areas.

Reference number 13 in FIG. 6 denotes aperture stop device. The aperture stop device has aperture stops 13a and 13b, as shown in FIG. 7 schematically in the embodiment, the illumination optical system 2 illuminates different areas 14a and 14b of the mask 4. The aperture stops 13a and 13b are controlled by a signal processing system, which will be described hereinafter, and act as adjustment means for opening angle to adjust the light flux of illumination light entering the objective lens OL.

Figure 8:
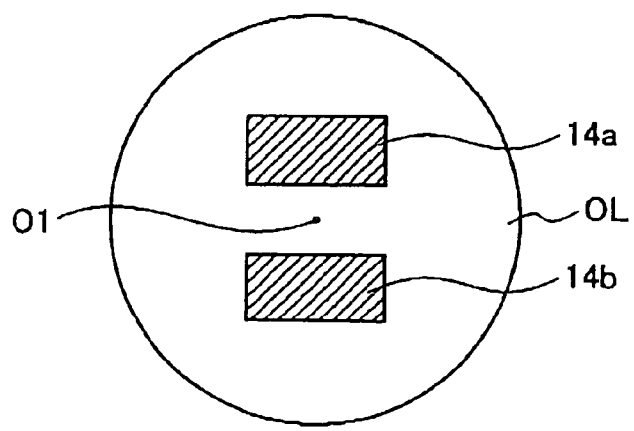
FIG. 8 is a plan view showing a positional relationship of the areas and an objective lens shown in FIG. 7.

The objective lens OL is disposed to face the mask 4. Detection optical systems 15 and 16 are also disposed to face the mask 4 through the objective lens OL. As schematically shown in FIG. 7, the detection optical system 15 has a focusing lens 18 receiving transmission-illumination light from the area 14a through the objective lens OL and forming a pattern image based on the area 14a on a detection sensor 17. The detection optical system 16 has a focusing lens 20 receiving the transmission-illumination light from the area 14b through the objective lens OL and forming a pattern image of the area 14b on a detection sensor 19. As schematically shown in FIG. 8, when viewing a positional relationship of the areas 14a and 14b in a plane perpendicular to an optical axis O1 of the objective lens OL, the area 14a and the area 14b are provided at symmetrical positions across the optical axis O1. Reference numeral 21 denoted in FIG. 7 is a total-reflection mirror for reflecting the illumination light from the area 14b toward the focusing lens 20.

The mask 4 is movable in a direction of optical axis (in a direction of arrows X-X') of the objective lens OL by a mask-position control mechanism 22 as shown in FIG. 1, thereby a distance L from the surface 5a of the silica glass 5 of the mask 4 to the center of the objective lens OL can be changed.

Figure 9:
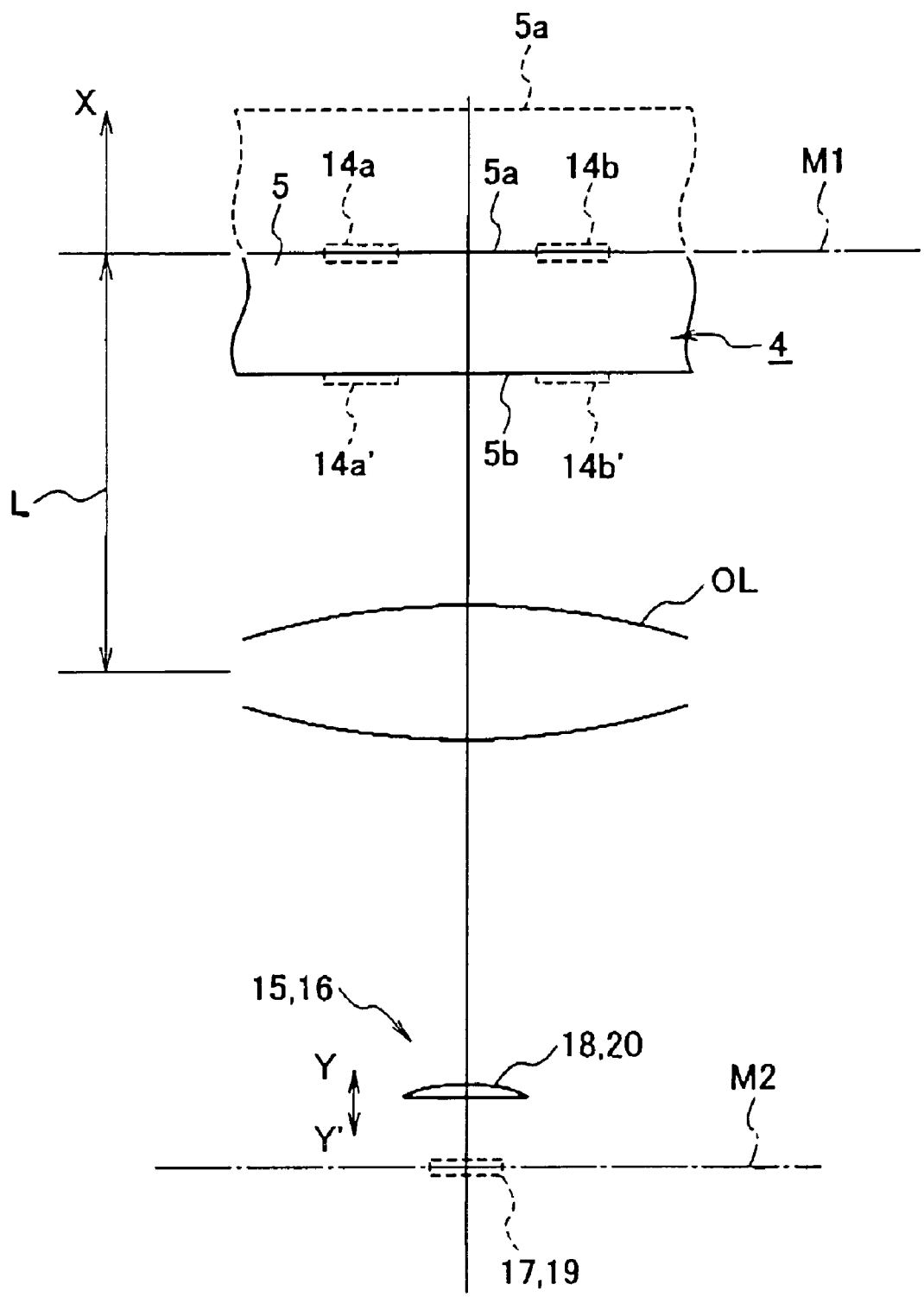
FIG. 9 is a diagram showing a relationship of pattern sites in a direction of film-thickness of the mask, an object plane and an image plane on a conceptual basis.

A conjugate relationship between an object plane M1 and an image plane M2 with respect to the objective lens OL is decided by optical performance of the objective lens OL. As schematically shown in FIG. 9, provided that the areas 14a and 14b on the surface 5a of the silica glass 5 are on the object plane M1 and the detection sensors 17 and 19 are on the image plane M2, pattern images corresponding to pattern sites existing at the areas 14a and 14b of the surface 5a of the silica glass 5 are formed on the detection sensors 17 and 19.

At this point, when the mask 4 is moved in the direction X along the optical axis O1 to allow a back surface 5b of the silica glass 5 to locate on the object plane M1, pattern images corresponding to pattern sites existing at areas 14a' and 14b' of the back surface 5b of the silica glass 5 are formed on the detection sensors 17 and 19.

More specifically, when the distance L between the mask 4 and the objective lens OL is changed by the mask-position control mechanism 22, a position of the object plane M1 in the film-thickness direction of the mask 4 is changed relatively. As a result, the pattern images of the pattern sites obtained by the detection sensors 17 and 19 are changed in the film-thickness direction.

Therefore, the mask-position control mechanism 22 functions as focusing-relation changing means for changing a focusing relation between the pattern sites in the film-thickness direction of the mask 4 and the pattern images obtained by the detection sensors 17 and 19, such that the pattern images obtained by the detection sensors 17 and 19 change the film-thickness direction of the mask 4.

Focusing control mechanisms 23 and 24 are provided in the detection optical systems 15 and 16, respectively, the focusing control mechanisms 23 and 24 act to control the focusing lenses 18 and 20 in the directions along the optical axes (in the direction of Y-Y'). When maintaining the distance L between the mask 4 and the objective lens OL constantly and adjusting the focusing lenses 18 and 20 in the optical axis directions, focusing positions of the pattern images by the focusing lenses 18 and 20, relative to image planes M2 are changed, thereby fine-adjustment of focuses of the pattern images formed on the detection sensors 17 and 19 is achieved. Therefore, the focusing control mechanism 23 and 24 also function as focusing relation changing means for changing the focusing relation between the pattern sites in the film-thickness direction of the mask 4 and the pattern images obtained by the detection sensors 17 and 19 so that the pattern images obtained by the detection sensors 17 and 19 change relative to the film-thickness direction of the mask 4.

The mask-position control mechanism 22, and focusing control mechanisms 23 and 24 are controlled by a signal-processing system 25. The signal-processing system 25 compares the pattern images obtained by the detection sensors 17 and 19 with a predetermined reference image on design, to inspect the presence or absence of defect in the mask 4.

In addition, the signal processing system 25 outputs the pattern images obtained by the detection sensors 17 and 19 to an image monitor (not shown) as image data. Accordingly, the mask-defect inspecting apparatus makes it possible to observe the pattern images on a screen of the image monitor.

Identification of type of defects is, for example, accomplished by comparing and determining a defect according to a pattern image obtained when the surface 5a of the silica glass 5 is in focus and a defect according to a pattern image obtained when the surface of the film-forming material is in focus.

There are various types of cross-sectional structures of the pattern 6 in the direction of film-thickness as shown in FIGS. 3A to 3C. Therefore, if data corresponding to the cross-sectional structures are previously stored in the signal processing system 25 and a distance of the mask 4 relative to the objective lens OL is decided on the basis of a cross-sectional structure of the mask 4 to be inspected, the inspection of defect can be executed promptly.

The focusing relation between the pattern sites in the film-thickness direction of the mask 4 and the pattern images obtained by the detection sensors 17 and 19 may also be decided by the distance of the mark 4 relative to the objective lens OL, based on inspection object information of whether to inspect the foreign matter attached on the mask 4 or to inspect a residual matter of the film-forming material forming the pattern.

Focal depth at the areas 14a and 14b changes because the aperture angle beside the object is adjusted by aperture stops 18a and 20a of the detection optical systems 15 and 16.

On the other hand, when the illumination light fluxes to the areas 14a and 14b are changed by adjusting the aperture stops 13a and 13b in the illumination optical system, because pattern images having sharp edges are obtained, clear and high accurate pattern images can be obtained by combining changes of the illumination light fluxes and the focal depth.

If a film-forming material remains in the pattern 6 at a location to be transmitted, in a design, the pattern image from the surface 6a of the film-forming material to the surface 5a of the silica glass 5 are obtained in a pattern image having a deep focal depth, but if the surface 6a of the Cr is in focus in a pattern image having a shallow focal depth, the pattern image of the surface 6a blurs and cannot be obtained. Therefore, when the defect in the pattern image having the shallow depth is not detected, it can be determined that the film-forming residue exists, even if the defect in the pattern image having the deep depth is detected.

Second Embodiment

Figure 10:
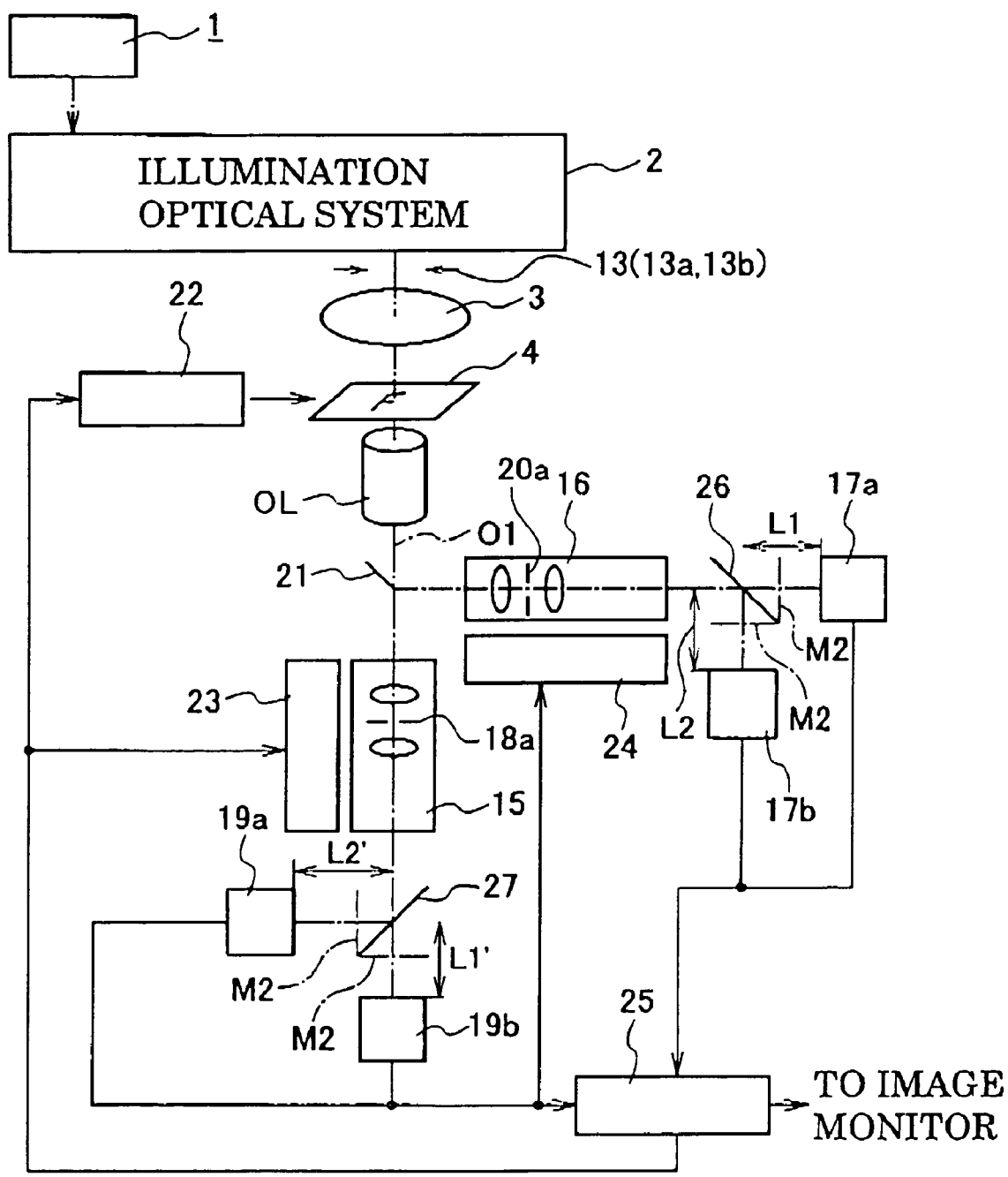
FIG. 10 is a diagram schematically showing an optical system in a second embodiment of the mask-defect inspecting apparatus according to the present invention

FIG. 10 is a diagram schematically showing a second embodiment of the mask-defect inspecting apparatus according to the present invention. In the mask-defect inspecting apparatus, half mirrors 26 and 27 are provided in the detection optical systems 15 and 16, respectively, for dividing the illumination light obtained through the focusing lenses 18 and 20 into two. Ahead of a direction of reflection of light on the half mirrors 26 and 27, there are provided detection sensors 17a, 17b, 19a and 19b, respectively.

A distance L1 from the detection sensor 17a to the half mirror 26 and a distance L2 from the detection sensor 17b to the half mirror 26 are different to another. Likewise, a distance L1' from the detection sensor 19a to the half mirror 27 and a distance L2' from the detection sensor 19b to the half mirror 27 are also different to another. Accordingly, the distances of the detection sensor 17a (19a) and the detection sensor 17b (19b) relative to the image planes M2 are different. In this way, when using a structure in which a plurality of detection sensors are provided on at least one of the detection optical systems such that the distances of the detection sensors relative to the image planes M2 are different from each other, each focal plane becomes different with regard to each of the detection sensors 17a (19a) and 17b (19b). As a result, a pattern image obtained by the detection sensor 17a (19a) and a pattern image obtained by the detection sensor 17b (19b) become images of pattern sites, which are different from each other in a direction of thickness of the mask 4. Hence, it is possible to identify promptly which of the pattern sites in the thickness direction of the mask 4 has the defect.

For example, as shown in FIG. 5C, it is possible to inspect whether the foreign matter attachment defect 11 exists on the surface 5a or in the groove 8 of the silica glass 5, promptly. Also, in this case, the focal depth can be changed by adjustment of the aperture stops 18a and 20a provided on the detection optical systems 15 and 16, independently.

Third Embodiment

Figure 11:
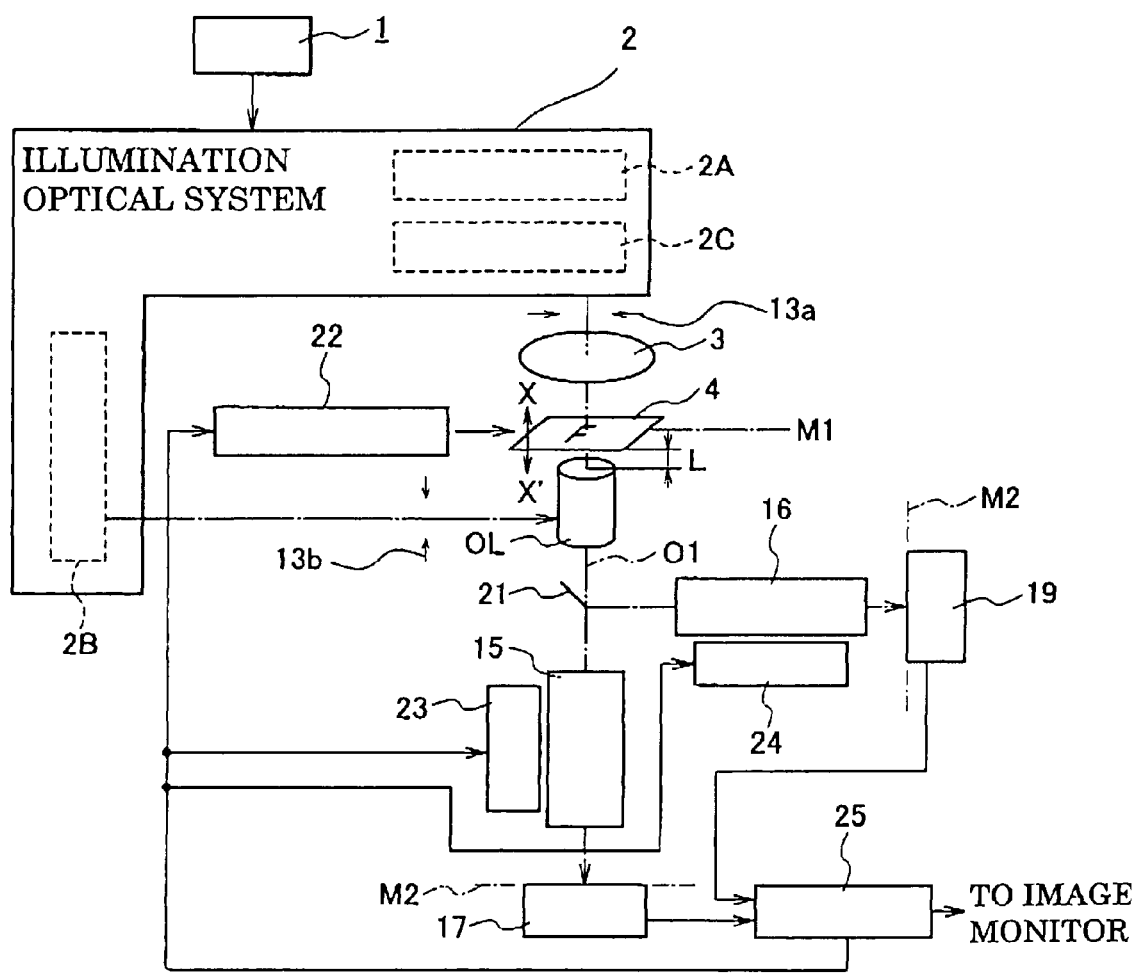
FIG. 11 is a diagram schematically showing an optical system in a third embodiment of the mask-defect inspecting apparatus according to the present invention

FIG. 11 is a diagram schematically showing a third embodiment of the mask-defect inspecting apparatus according to the present invention. In the mask-defect inspecting apparatus, the illumination optical system 2 includes a transmission-type illumination optical system 2A for illuminating the mask 4 from the surface 5a of the silica glass 5 of the mask 4 and a reflection-type illumination optical system 2B for illuminating the mask 4 from the back surface 5b of the silica glass 5 of the mask 4. In this embodiment, the transmission-type illumination optical system 2A is provided with an illumination light switch-over mechanism 2C for carrying out switching over of the illumination light between the transmission-illumination light and the reflection-illumination light.

Figure 12:
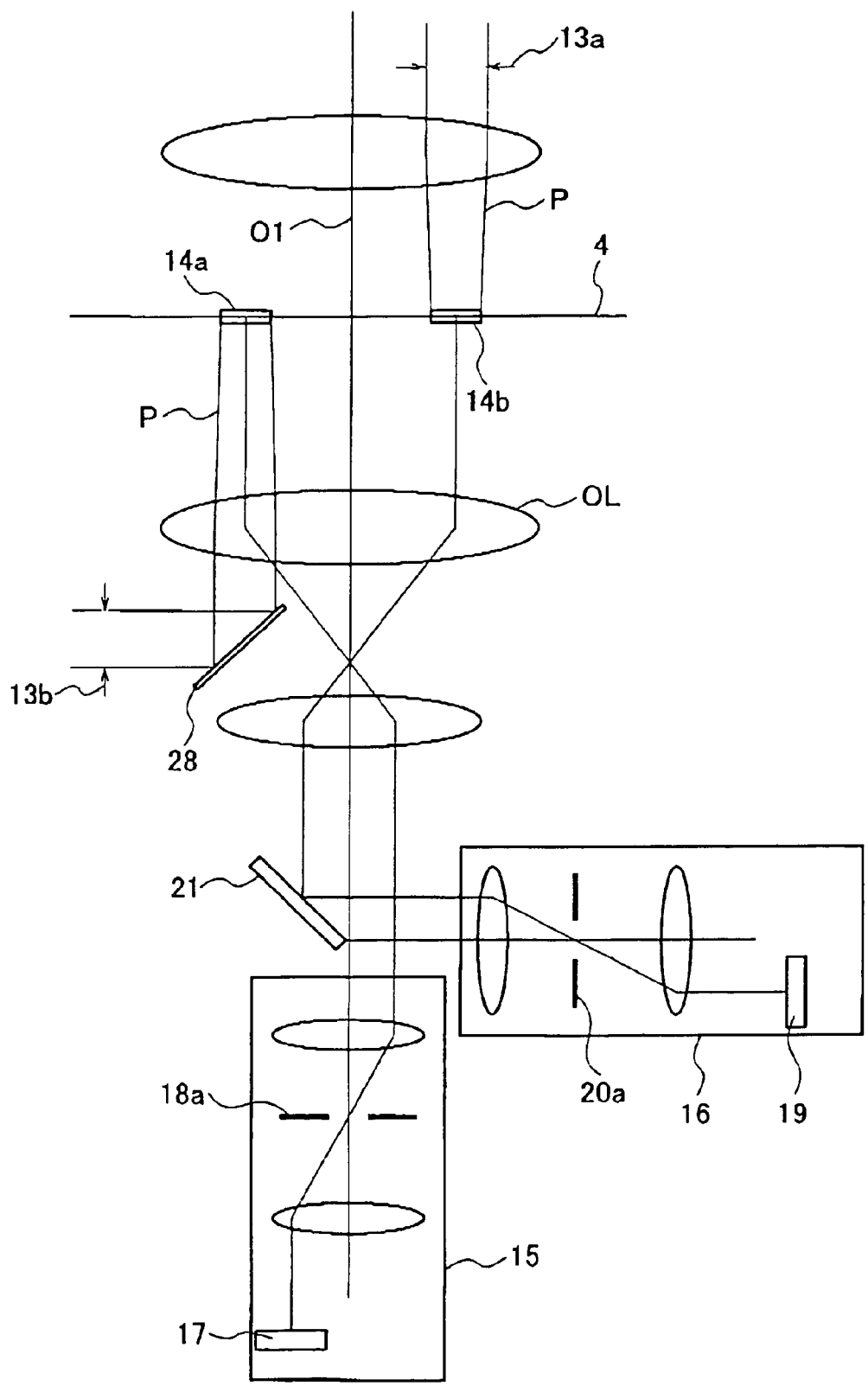
FIG. 12 is a diagram schematically showing a relationship between detection optical systems and illumination areas shown in FIG. 11.

As shown in FIG. 12, the reflection-type illumination optical system 2B includes a light-focusing lens (not shown) and a reflection mirror 28 for reflecting the illumination light toward the objective lens OL. The reflection-type illumination optical system 2B illuminates the mask 4 for example by the Kohler illumination method. The light-focusing lens forms a light source image of the light source 1 on a focal plane of the objective lens OL. The objective lens OL converts its illumination light into a parallel light flux to illuminate the area 14a as the reflection-illumination light.

The transmission-type illumination optical system 2A includes the aperture stop 13a disposed in the front of the condenser lens 3, and the reflection-type illumination optical system 2B includes the aperture stop 13b disposed in the back of the objective lens OL.

The detection optical system 15 is disposed to face the area 14a through the objective lens OL, and the detection optical system 16 is disposed to face the area 14b through the objective lens OL. The detection optical system 16 functions as a transmission-detection optical system for forming a pattern image of the area 14b illuminated by the transmission-illumination light on the detection sensor 19, and the detection optical system 15 functions as a reflection-detection optical system for forming a pattern image of the area 14a illuminated by the reflection-illumination light on the detection sensor 17.

The aperture stop 18a for adjusting an amount of light beside the image is disposed in the front of the focusing lens 18 of the detection optical system 15, and the aperture stop 20a for adjusting an amount of light beside the image is disposed in the front of the focusing lens 20 of the detection optical system 16. The aperture stops 18a and 20a are adjusted independently, when they are adjusted suitably, the focal depth is changed similarly to the first and second embodiments, the aperture stops also functions as means for adjusting aperture angles.

It is not easy to distinguish images when illuminating a same area simultaneously by the transmission-type illumination and the reflection-type illumination and taking the pattern images in the same detection optical system, since the pattern images overlap with each other. However, when the detection optical systems 15 and 16 are used as the transmission-detection optical system and the reflection-detection optical system, and at the same time, when the different areas 14a and 14b are illuminated, it is possible to retrieve the pattern images simultaneously without the pattern images being overlapped. Therefore, it is possible to achieve promptly the identification as to whether the foreign matter is attached on the mask 4 or the film-forming material for forming the pattern remains on the mask 4.

As well as in this embodiment, the focusing relation between the pattern sites in the film-thickness direction of the mask 4 and the pattern images obtained by the detection sensors 17 and 19 may be decided by the distance L of the mask 4 relative to the objective lens OL, based on the inspection object information of whether to inspect the foreign matter attached on the mask 4 or to inspect the residual matter of the film-forming material forming the pattern.

More specifically, if a position of the surface 5a of the silica glass 5 and a position of the surface 6a of the film-forming material are calculated by calibration carried out before the inspection and positions in focus of the detection sensors 17 and 19 are previously set on the basis of whether the object to be inspected is the residual matter of the film-forming material attached on the mask 4 or the foreign matter attached on the mask 4, it is possible to ensure the prompt inspection of the defect.

In addition, if the illumination optical system 2A is switched-over from the illumination type of transmission-illumination to the illumination type of reflection-illumination by use of the illumination light switch-over mechanism 2C, it is possible to retrieve the pattern image according to the transmission-illumination and the pattern image according to the reflection-illumination with the same detection optical system 16 with regard to the same area 14b, hence by comparing those pattern images, it is possible to achieve the identification of the defect more easily.

Furthermore, when the aperture stops 13a, 13b in the illumination optical system 2, and the aperture stops 18a, 20a in the detection optical systems 15 and 16 are adjusted suitably, because a sigma or .sigma. value of the illumination changes, and a manner for viewing the pattern images changes, it is possible to achieve detailed identification of the inspection for the defect, conveniently.

Here, the σ value of the illumination corresponds to a value obtained by dividing the aperture angle of the illumination optical system 2 by the aperture angles of the detection optical systems, and dimensionless value. When σ equals to 1 (σ=1), the values of the aperture angles of the illumination and detection optical systems 2 and 15,16 are the same.

The settings of the aperture angle and the a value may be executed in a calibration process before the inspection for the defect, by use of the signal processing system 25.

In the third embodiment, because the σ value of the illumination is changed by adjusting the aperture stops 13a, 13b, and 18a, 18b independently when inspecting the different areas simultaneously by use of both the transmission-detection optical system and the reflection-detection optical system, reflection inspection and transmission inspection can be achieved promptly in the in performing the identification of the inspection of the defect in detail.

Meanwhile, the transmission-detection optical system and the reflection-detection optical system are disposed to face the back surface 5b of the silica glass 5 through the objective lens OL, the pattern 6 may be provided on the surface 5a or the back surface 5b.

Because a known structure can be utilized for the illumination light switch-over mechanism 2C, a detailed structure thereof is omitted.

Fourth Embodiment

Figure 13:
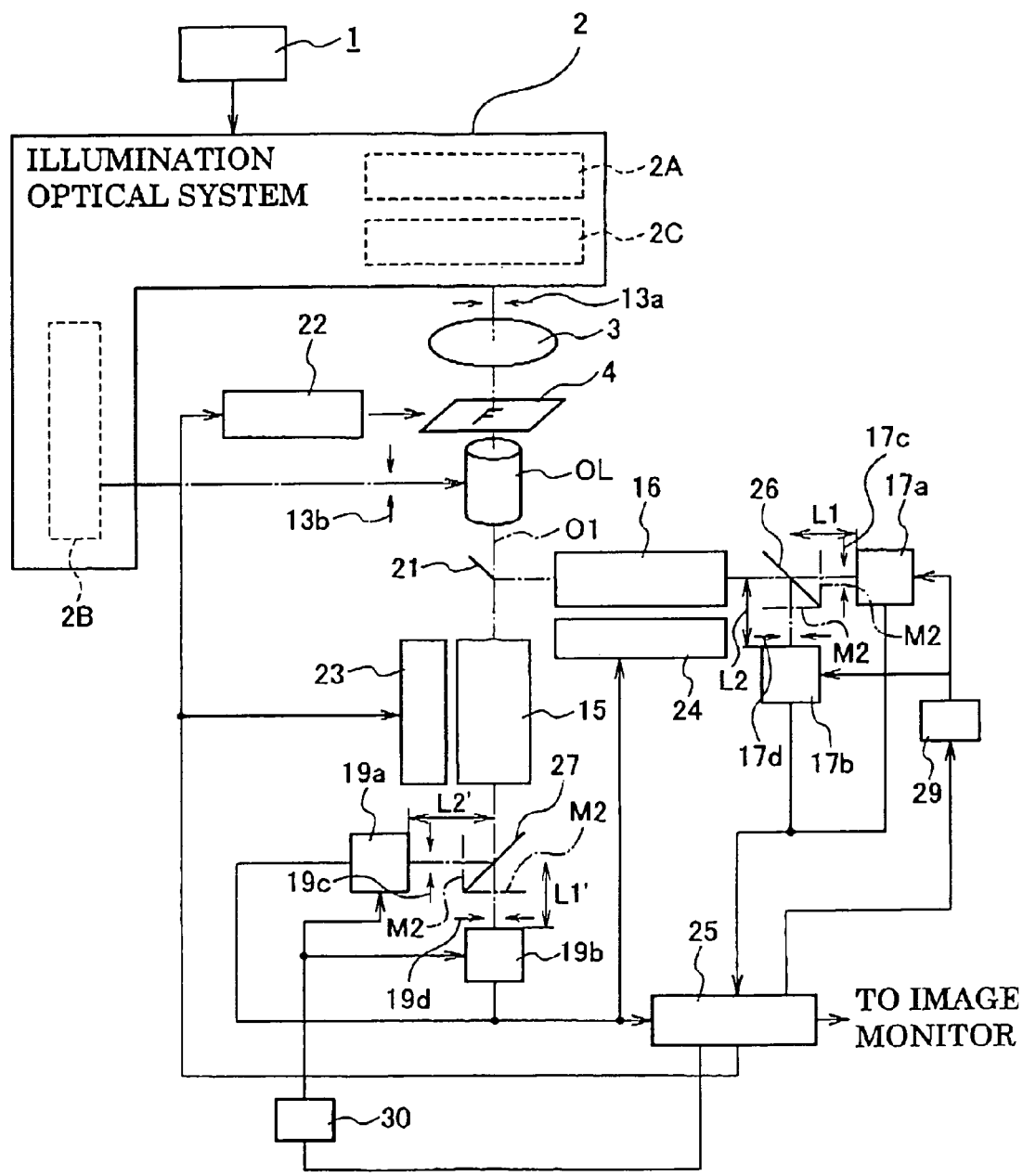
FIG. 13 is a diagram schematically showing an optical system in a fourth embodiment of the mask-defect inspecting apparatus according to the present invention

FIG. 13 is a diagram schematically showing a fourth embodiment of the mask-defect inspecting apparatus according to the present invention. In the mask-defect inspecting apparatus, the detection optical systems 15 and 16 are provided with the half mirrors 26 and 27, respectively, for dividing the illumination light obtained through the focusing lenses 18 and 20 into two, similarly to the second embodiment. Ahead of the directions of light reflected on the half mirrors 26 and 27, there are provided the detection sensors 17a, 17b, and 19a, 19b, respectively. The distance L1 from the detection sensor 17a to the half mirror 26 and the distance L2 from the detection sensor 17b to the half mirror 26 are different from each other, similarly to the second embodiment. Furthermore, the distance L1' from the detection sensor 19a to the half mirror 27 and the distance L2' from the detection sensor 19b to the half mirror 27 are also different from each other.

In the fourth embodiment, the detection sensors 17a, 17b and 19a, 19b are movable in the optical axis directions of the detection optical systems 15 and 16 by sensor moving mechanisms 29 and 30.

Moreover, in the fourth embodiment, the aperture stops 17c, 17d, and 19c, 19d are provided in the front of the detection sensors 17a, 17b and 19a, 19b, in place of provision of the aperture stops 18a and 20a in the front of the focusing lenses 18 and 20. It is possible to save the trouble of computation if the values of the aperture angles of the aperture stops 13a, 13b, 17c, 17d, 19c, 19d are input previously in the signal processing system 25 based on the data on a structure of the mask 4.

According to this embodiment, when the detection sensors 17a, 17b, 19a and 19b are moved in the optical axis directions in such a manner that the distance L between the mask 4 and the objective lens OL is maintained constantly, and the positional relationships of the focusing lenses 18 and 20 relative to the objective lens OL are maintained constantly, the focusing positions of pattern images relative to the image planes M2 are changed by the detection sensors 17a, 17b, 19a and 19b, thereby fine adjustment for focuses of the pattern images formed on the detection sensors 17a, 17b, 19a and 19b is achieved.

Therefore, in the fourth embodiment, the sensor moving mechanisms 29 and 30 function as focusing relation changing means or mechanism for changing the relation of focusing between the pattern sites in the film-thickness direction of the mask 4 and the pattern images obtained by the detection sensors 17a, 17b, 19a and 19b so that the pattern images obtained by the detection sensors 17a, 17b, 19a and 19b change relative to the film-thickness direction of the mask 4.

In the above-mentioned embodiments, the focusing relation changing means is structured by the mask-position control mechanism 22 which changes the distance L between the objective lens OL and the mask 4 by moving the mask 4 relative to the objective lens OL in the direction of optical axis of the objective lens OL. However, the focusing relation changing means may be structured by an objective lens moving mechanism for moving the objective lens OL in the optical axis direction.

Although the preferred embodiments of the present invention have been described, the present invention is not limited to the embodiments, various changes and modifications can be made to the embodiments.

What is claimed is:

1. A mask-defect inspecting apparatus, comprising:
a plurality of illumination optical systems for illuminating different areas on a mask on which a pattern is formed, one of the plurality of illumination optical systems being a transmission-type illumination optical system to illuminate the mask and the other of the plurality of illumination optical systems being a reflection-type illumination optical system to illuminate the mask;
each of the illumination optical systems includes an aperture stop, which are independently adjustable;
an objective lens disposed to face the mask;
at least a pair of detection optical systems each having a detection sensor to form an image of the pattern and for receiving illumination light from each of the different areas through the objective lens; and
an illumination light switch-over mechanism configured to carry out switching over of the illumination light between the transmission-type illumination optical system and the reflection-type illumination optical system;
each of the detection optical systems including a mechanism for adjusting an angle of an aperture, wherein each of the mechanisms is capable of adjusting the angle of the aperture independently of the other;
each of the detection optical systems including a movable focusing lens to receive light passing through the objective lens;
each of the detection optical systems including a focusing control mechanism to control movement of the focusing lens,
wherein one of the detection optical systems comprises a transmitted-type detection optical system for receiving light from the area illuminated by the transmitted illumination light and the other of the detection optical systems comprises a reflection-detection optical system for receiving an image from the area illuminated by the reflecting illumination light,
wherein a distance of one of the detection sensors from an image plane is different from a distance of another one of the detection sensors from the image plane.

2. A mask-defect inspecting apparatus, comprising:
a plurality of illumination optical systems for illuminating different areas on a mask on which a pattern is formed, one of the plurality of illumination optical systems being a transmission-type illumination optical system to illuminate the mask and the other of the plurality of illumination optical systems being a reflection-type illumination optical system to illuminate the mask;
each of the illumination optical systems includes an aperture stop, which are independently adjustable;
an objective lens disposed to face the mask;
at least a pair of detection optical systems each having a detection sensor to form an image of the pattern and for receiving illumination light from each of the different areas through the objective lens; and
an illumination light switch-over mechanism configured to carry out switching over of the illumination light between the transmission-type illumination optical system and the reflection-type illumination optical system;
each of the detection optical systems including a mechanism for adjusting an angle of an aperture, wherein each of the mechanisms is capable of adjusting the angle of the aperture independently of the other;
each of the detection optical systems including a movable focusing lens to receive light passing through the objective lens;
each of the detection optical systems including a focusing control mechanism to control movement of the focusing lens,
wherein one of the detection optical systems comprises a transmitted-type detection optical system for receiving light from the area illuminated by the transmitted illumination light and the other of the detection optical systems comprises a reflection-detection optical system for receiving an image from the area illuminated by the reflecting illumination light,
wherein each of the detection sensors is movable in an optical direction of each of the detection optical systems by a sensor moving mechanism.

* * * * *